(12) United States Patent
Gauthier et al.

(10) Patent No.: US 7,541,384 B2
(45) Date of Patent: Jun. 2, 2009

(54) MESALAMINE SUPPOSITORY

(75) Inventors: Carl Gauthier, Quebec (CA); Yves Dumoulin, Quebec (CA); David Powell, Loudon, TN (US)

(73) Assignee: Axcan Pharma Inc., Mont-St-Hilaire, Quebec (CA)

( * ) Notice: Subject to any disclaimer, the term of this patent is extended or adjusted under 35 U.S.C. 154(b) by 0 days.

(21) Appl. No.: 12/245,648

(22) Filed: Oct. 3, 2008

(65) Prior Publication Data

US 2009/0022793 A1    Jan. 22, 2009

Related U.S. Application Data

(63) Continuation of application No. 12/135,103, filed on Jun. 6, 2008, now abandoned.

(60) Provisional application No. 60/943,029, filed on Jun. 8, 2007.

(51) Int. Cl.
| | |
|---|---|
| *A01N 33/02* | (2006.01) |
| *A01N 37/36* | (2006.01) |
| *A01N 37/12* | (2006.01) |
| *A01N 37/44* | (2006.01) |
| *A61K 31/135* | (2006.01) |
| *A61K 31/60* | (2006.01) |
| *A61K 31/195* | (2006.01) |
| *A61F 13/00* | (2006.01) |

(52) U.S. Cl. .................. 514/649; 514/159; 514/567; 514/953; 424/433

(58) Field of Classification Search ............... 514/567, 514/159, 649, 953; 424/433
See application file for complete search history.

(56) References Cited

U.S. PATENT DOCUMENTS

| | | | |
|---|---|---|---|
| 3,689,514 A | * | 9/1972 | Neissner et al. ............. 554/227 |
| 4,211,777 A | | 7/1980 | Chambers et al. |
| 4,298,595 A | | 11/1981 | Parkinson et al. |
| 4,374,932 A | | 2/1983 | Pitzele et al. |
| 4,540,685 A | | 9/1985 | Bauer et al. |
| 4,632,921 A | | 12/1986 | Bauer et al. |
| 4,699,902 A | | 10/1987 | Bauer et al. |
| 5,500,221 A | | 3/1996 | Murata et al. |
| 5,508,037 A | | 4/1996 | ElSohly |
| 5,539,000 A | * | 7/1996 | Leonard ..................... 514/682 |
| 5,629,012 A | | 5/1997 | Halskov et al. |
| 5,716,648 A | | 2/1998 | Halskov et al. |
| 6,136,337 A | | 10/2000 | Kondo et al. |
| 6,139,863 A | | 10/2000 | Yokomachi et al. |
| 6,210,698 B1 | | 4/2001 | Yamazaki et al. |
| 6,326,364 B1 | | 12/2001 | Lin et al. |
| 6,720,001 B2 | | 4/2004 | Chen et al. |
| 6,903,082 B2 | | 6/2005 | Ekwuribe et al. |
| 7,250,445 B1 | | 7/2007 | Ehrenpreis |
| 7,312,243 B1 | | 12/2007 | Pravda |
| 7,326,809 B2 | | 2/2008 | Wallace et al. |
| 7,341,741 B1 | | 3/2008 | Sachetto et al. |
| 2002/0037855 A1 | | 3/2002 | Stanislaus |
| 2005/0159396 A1 | | 7/2005 | Harty |
| 2006/0003972 A1 | | 1/2006 | Wallace et al. |
| 2006/0127503 A1 | | 6/2006 | Harly |
| 2006/0223787 A1 | | 10/2006 | Devane et al. |
| 2007/0122384 A1 | | 5/2007 | Ohrstrom |
| 2007/0167416 A1 | | 7/2007 | Johnson |
| 2007/0213296 A1 | | 9/2007 | Zhang |
| 2007/0240236 A1 | | 10/2007 | Xia |
| 2007/0254050 A1 | | 11/2007 | Quart et al. |
| 2008/0008740 A1 | | 1/2008 | Franc et al. |
| 2008/0020018 A1 | | 1/2008 | Moodley et al. |
| 2008/0031983 A1 | | 2/2008 | Quart et al. |
| 2008/0076744 A1 | | 3/2008 | Schreiber |
| 2008/0107650 A1 | | 5/2008 | Tartaglia et al. |

FOREIGN PATENT DOCUMENTS

JP    2008-024713    2/2008

OTHER PUBLICATIONS

Marteau et al. Gut, 1998, vol. 42, No. 2, pp. 195-199.*
Hanauer et al. Abstract, American Journal of Gastroenterology, vol. 95, No. 7, pp. 1749-1754 (2000).
Physicians Desk Reference (1999) for Rowasa® pp. 3126-3128.
CANASA® Package Insert, Axcan Proposed Nov. 4, 2004.
Zhongguo Linchuang Yaolixue Zazhi, vol. 20, No. 2, pp. 126-130 (2004).
MacDermott, R. P., J Gastroenterology, 31:907:-916 (1996).
Mesalamine Suppositories; www.drugs.com/cdi/mesalamine-suppositories.html; Accessed Jun. 2, 2008.
Declaration of David R. Powell, Ph.D.

* cited by examiner

*Primary Examiner*—Sreeni Padmanabhan
*Assistant Examiner*—Samira Jean-Louis
(74) *Attorney, Agent, or Firm*—Darby & Darby P.C.

(57) ABSTRACT

The present invention relates to a mesalamine rectal suppository designed to provide improved comfort of use. One embodiment of the invention is a mesalamine rectal suppository containing mesalamine and one or more pharmaceutically acceptable excipients, wherein the drug load of the suppository ranges from 35% to 50%. Another embodiment of the invention is a mesalamine rectal suppository containing from about 850 to about 1150 mg mesalamine and one or more pharmaceutically acceptable excipients, wherein the total weight of the suppository ranges from about 2250 to about 2700 mg. Yet another embodiment of the invention is a mesalamine rectal suppository comprising mesalamine having a tap density ranging from about 600 to about 800 g/L (as measured by USP <616>) and a hard fat having an ascending melting point of 32 to 35.5° C. Methods of preparing and methods of treatment with mesalamine suppositories are also provided. The invention further provides a method of determining a dissolution parameter (such as dissolution rate) of a mesalamine rectal suppository, such as a 1 g mesalamine suppository, by measuring its dissolution with USP Apparatus #2 at 40° C. and a paddle rotation speed of 125 rpm in 0.2 M phosphate buffer at a pH of 7.5.

16 Claims, 10 Drawing Sheets

MESALAMINE
TAPPED DENSITY: VISCOSITY CORRELATION

MESALAMINE
TAPPED DENSITY: VISCOSITY CORRELATION
(Combined Data)

MESALAMINE SUPPOSITORY DISSOLUTION

MESALAMINE SUPPOSITORY DISSOLUTION

MESALAMINE SUPPOSITORY DISSOLUTION

42% and 44% dissolution profile results

MESALAMINE SUPPOSITORY

This application is a continuation of U.S. application Ser. No. 12/135,103, filed Jun. 6, 2008, and claims the benefit of provisional application 60/943,029, filed Jun. 8, 2007.

FIELD OF THE INVENTION

The present invention relates to a mesalamine suppository designed to provide improved comfort of use, a method for manufacturing it, and methods for treating ulcerative colitis, such as active ulcerative proctitis, with it as well as a method of measuring a dissolution parameter of a mesalamine suppository.

BACKGROUND OF THE INVENTION

Inflammatory bowel diseases (IBD), such as Crohn's disease and ulcerative colitis (UC), are characterized by chronic, relapsing intestinal inflammation. Crohn's disease and UC are believed to involve a dysregulated immune response to gastrointestinal (GI) tract antigens, a mucosal barrier breach, and/or an adverse inflammatory reaction to a persistent intestinal infection. In normal people, the GI tract luminal contents and bacteria constantly stimulate the mucosal immune system, and a delicate balance of pro-inflammatory and anti-inflammatory cells and molecules maintains the integrity of the GI tract, without eliciting severe and damaging inflammation [MacDermott, R. P., J Gastroenterology, 31:907:-916 (1996)]. It is unknown how the IBD inflammatory cascade begins, but constant GI antigen-dependent stimulation of the mucosal and systemic immune systems perpetuates the inflammatory cascade and drives lesion formation.

UC is a non-specific inflammatory disease of the colon that is of unknown cause and is characterized by diarrhea with discharge of mucus and blood, cramping abdominal pain, and inflammation and edema of the mucous membrane with patches of ulceration. UC limited to the rectum is known as ulcerative proctitis. People suffering from chronic UC affecting the whole colon have an increased risk of colonic cancer. Furthermore, when medical therapy fails, surgical resection of affected bowel may be necessary.

In patients with more extensive disease, blood loss from the inflamed intestines can lead to anemia, and may require treatment with iron supplements or even blood transfusions. Although infrequent, the colon can acutely dilate to a large size when the inflammation becomes very severe. This condition is called toxic megacolon. Patients with toxic megacolon are extremely ill with fever, abdominal pain and distention, dehydration, and malnutrition. Unless the patient improves rapidly with medication, surgery is usually necessary to prevent colon rupture and high risk of death.

Mesalamine, 5-aminosalicylic acid (5-ASA), is often used to treat UC and is effective in reducing disease symptoms and the incidence of relapse in UC. While mesalamine is available in oral form, intrarectal administration of it has several advantages. For example, rectal administration of a drug avoids some side-effects, such as gastrointestinal disorders, due to oral administration. Lower doses of a drug can be administered rectally to obtain the same therapeutic effect as that attained with a higher dose oral formulation. Since, unlike the GI tract, acids and enzymes scarcely exist in the rectum, the drug remains substantially intact before absorption. Furthermore, because the majority of drug absorbed from the rectum first moves with blood streams which do not pass through the liver, less of the absorbed drug is metabolized and inactivated by the liver in contrast to oral administration in which the absorbed drug generally moves with blood streams which flow through the liver. The absorption of a drug orally administered may also be affected by whether it is administered before or after each meal or between meals. There is no such food effect when drugs are administered intrarectally. Intrarectal administration can be performed even during nausea, vomiting or unconsciousness, or after surgical operation.

A 1 g mesalamine suppository of a substantial size (3 g) is currently marketed in the U.S. by Axcan Scandipharm Inc. as CANASA® for the treatment of active ulcerative proctitis.

There is a need for mesalamine suppositories which provide increased comfort of use.

SUMMARY OF THE INVENTION

The present inventors have discovered that the size of a mesalamine suppository can be drastically reduced (for example, by over 20% by weight) and the melting point lowered without a substantial adverse effect on its dissolution profile or its overall therapeutic efficacy. The combination of a smaller suppository and a lower melting temperature provides increased comfort of use. The inventors discovered that this result can be obtained by increasing the tap density of the mesalamine and, preferably, also lowering the melting point of the suppository base.

Generally when the drug load of a mesalamine suppository is increased, so too is its viscosity. If the viscosity of the mesalamine suspension is too high, it cannot be cast into a suppository having good therapeutic properties. The inventors have surprisingly found that the viscosity of the mesalamine suspension can be decreased by increasing the tap density of the mesalamine.

One embodiment of the present invention is a mesalamine rectal suppository comprising mesalamine and one or more pharmaceutically acceptable excipients, wherein the drug load of the suppository ranges from about 35% to about 50% and preferably from about 37% to about 46%. The suppository may include from about 850 to about 1150 mg mesalamine, and preferably includes about 950 mg to about 1050 mg mesalamine (and even more preferably about 1000 mg mesalamine). The mesalamine suppository may further include a suppository base, such as hard fat (e.g., hard fat NF).

Another embodiment of the invention is a mesalamine rectal suppository comprising from about 850 to about 1150 mg mesalamine and one or more pharmaceutically acceptable excipients, wherein the total weight of the suppository ranges from about 2250 to about 2700 mg. Preferably, the total weight of the suppository ranges from about 2250 to about 2500 mg. The amount of mesalamine in the suppository preferably ranges from about 950 mg to about 1050 mg and more preferably is about 1000 mg. The mesalamine suppository may further include a suppository base, such as hard fat (e.g., hard fat NF).

The mesalamine in each of the aforementioned suppositories preferably has a tap density ranging from about 600 to about 800 g/L (as measured by USP <616>). According to a preferred embodiment, the mesalamine in the aforementioned suppositories is dispersed in a low melting suppository base (i.e., a suppository base having an ascending melting point of no more than 35.5° C.). A preferred low melting suppository base is hard fat having an ascending melting point of 32 to 33.5° C. (e.g., Witepsol® H 12 available from Sasol Germany GmbH of Witten, Germany). Another suitable low melting suppository base is hard fat having an ascending melting point of 33.5 to 35.5° C. (e.g., Witepsol® H-15 available from Sasol Germany GmbH). The dispension is preferably substantially homogenous.

Yet another embodiment of the invention is a mesalamine rectal suppository comprising mesalamine having a tap density ranging from about 600 to about 800 g/L (as measured by USP <616>) and a hard fat having an ascending melting point of 32 to 35.5° C. Typically, the mesalamine is dispersed in the hard fat. According to one preferred embodiment, the hard fat has an ascending melting point of 32 to 33.5° C. Preferably, such a dispension is substantially homogenous. The weight ratio of mesalamine to hard fat preferably ranges from about 1:2 to about 1:1.25.

Preferably, the aforementioned suppositories each release at least about 75% by weight of the mesalamine contained in the suppository within 2 hours of dissolution as measured with USP Apparatus #2 at 40° C., a paddle rotation speed of 125 rpm, and 3 sinker turns in 0.2 M phosphate buffer at a pH of 7.5. In one embodiment, at least about 80, 90, or 95% by weight of the mesalamine is dissolved within 2 hours. According to another embodiment, at least about 80 or 90% by weight of the mesalamine is dissolved within 1 hour. According to yet another embodiment, at least 90% by weight of the mesalamine is dissolved within 30 minutes.

Yet another embodiment is a method of treating ulcerative colitis, such as active ulcerative proctitis, in a patient in need thereof by administering to the patient a mesalamine rectal suppository of the present invention. Preferably, the mesalamine suppository is administered once a day and more preferably once a day at bedtime. The suppository is also preferably retained for one to three hours or longer, if possible. The treatment can be brief, for example, once daily for three to twenty-one days, or can be longer, for example, once daily for three to six weeks.

Yet another embodiment is a method of determining a dissolution parameter (such as dissolution rate or amount of drug dissolved after a specified period of time) of a mesalamine rectal suppository, such as a 1 g mesalamine suppository, by measuring its dissolution with USP Apparatus #2 at 40° C. and a paddle rotation speed of 125 rpm in 0.2 M phosphate buffer at a pH of 7.5. According to a preferred embodiment, a sinker is lightly coiled around the suppository, for example with only 3 turns of wire helix. This dissolution method produces results which are significantly more reliable and less variable than those produced by other dissolution methods, such as methods 1 and 3 discussed in Examples 1 and 2.

Yet another embodiment is a method of preparing a mesalamine rectal suppository by (A) providing a mesalamine rectal suppository, and (B) measuring the dissolution rate of the suppository with USP Apparatus #2 at 40° C. and a paddle rotation speed of 125 rpm in 0.2 M phosphate buffer at a pH of 7.5. According to a preferred embodiment, a sinker is lightly coiled around the suppository, for example, with only 3 turns of wire helix. Step (B) may include determining whether the suppository releases at least about 75% by weight of the mesalamine within 2 hours of dissolution.

Yet another embodiment is a method of preparing a batch of mesalamine rectal suppositories (i.e., 2 or more suppositories) by (A) providing a batch of mesalamine rectal suppositories; and (B) measuring the dissolution rate of at least one suppository from the batch with USP Apparatus #2 at 40° C. and a paddle rotation speed of 125 rpm in 0.2 M phosphate buffer at a pH of 7.5. According to a preferred embodiment, a sinker is lightly coiled around the suppository, for example, with only 3 turns of wire helix. Preferably, step (B) includes determining whether the suppository releases at least about 75 or 80% by weight of the mesalamine within 2 hours of dissolution (Q=75% as described in USP 711 (30$^{th}$ Ed.), the section entitled "immediate-release dosage forms"). If the suppository does not meet the dissolution criterion, the batch of suppositories can be discarded.

Yet another embodiment is a method of preparing a mesalamine rectal suppository by preparing the suppository from mesalamine having a tap density ranging from about 600 to about 800 g/L with a suppository base, such as a hard fat, having an ascending melting point of 32 to 33.5° C. The inventors have found that the viscosity of a molten mixture containing mesalamine varies significantly depending on the tap density of the mesalamine used to form the molten mixture. A molten mixture having a high viscosity (e.g., greater than 5000 cps) has been found to have flow problems during suppository filling and caused small entrapped air bubbles to be molded into the surface of the suppository resulting in an aesthetically less desirable product. The suppository may, for example, be prepared by (A) mixing the mesalamine having the aforementioned tap density with a suppository base having the aforementioned melting point, and (B) molding the mixture.

According to one embodiment, the mesalamine suppository is prepared by (A) melting the suppository base, e.g., to form a molten solution, (B) adding mesalamine to the melted suppository base, and (C) molding the mixture.

DETAILED DESCRIPTION OF THE INVENTION

Definitions

Figure 1:
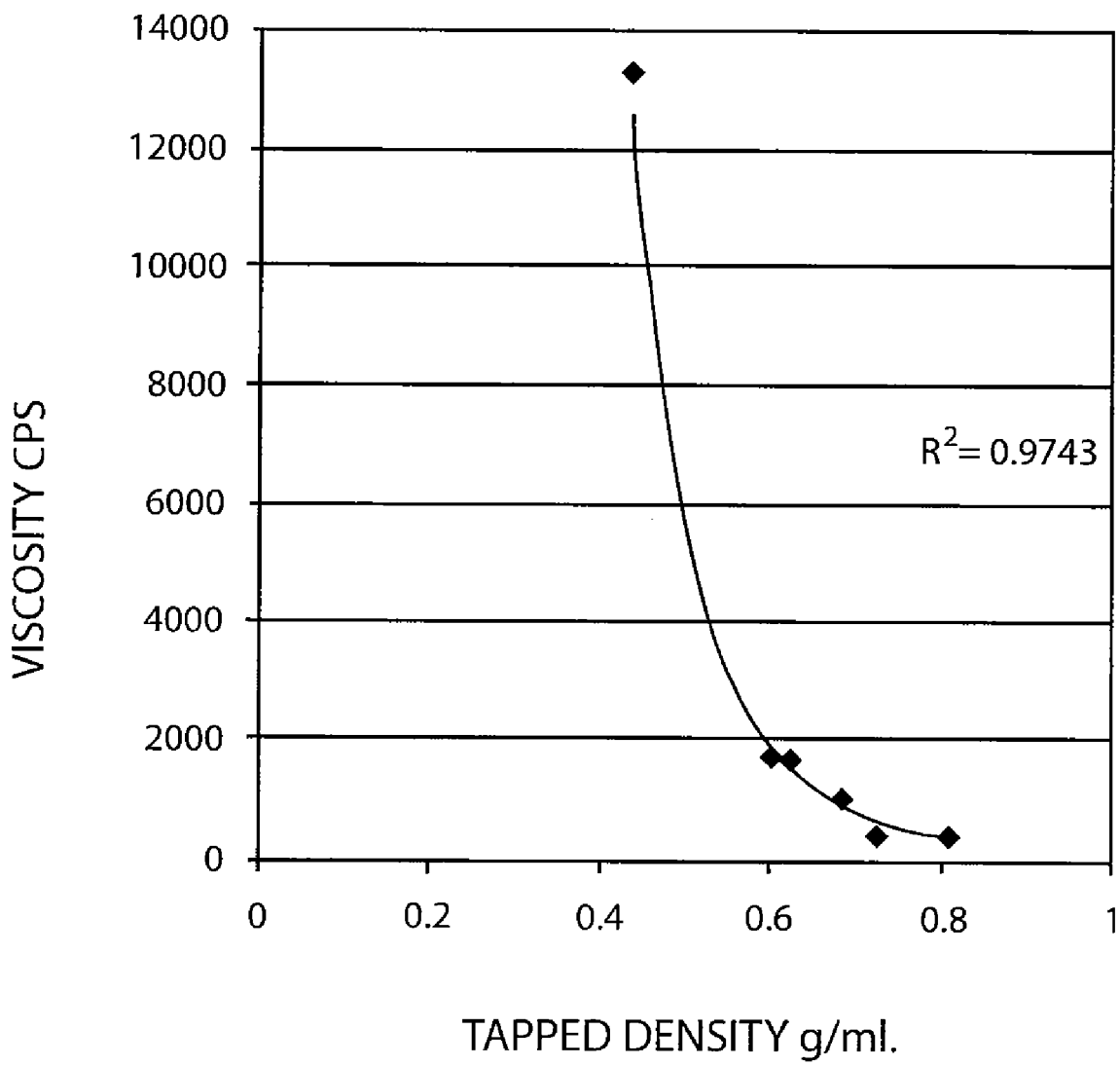
FIG. 1 is a graph showing the viscosity of the molten mixtures prepared in Example 3 versus the tap densities of the mesalamine used to prepare the molten mixtures.

The term "mesalamine" refers to 5-aminosalicylic acid (5-ASA). According to one embodiment, the mesalamine has the following particle size distribution: X10 of about 5 to about 11 μm, X50 of about 25 to about 45 μm, and X90 of about 85 to about 100 μm.

The term "drug load" refers to the weight percentage of mesalamine based on the total weight of the suppository.

As used herein, the term "patient" refers to any mammal and preferably a human. The patient to be treated with mesalamine may in fact be any patient of the human population, male or female, which may be divided into children, adults, or elderly. Any one of these patient groups relates to an embodiment of the invention.

As used herein, the term "treating" refers to preventing or delaying the appearance of clinical symptoms of a disease or condition in a patient that may be afflicted with or predisposed to the disease or condition, but does not yet experience or display clinical or subclinical symptoms of the disease or condition. "Treating" also refers to inhibiting the disease or condition, i.e., arresting or reducing its development or at least one clinical or subclinical symptom thereof. "Treating" further refers to relieving the disease or condition, i.e., causing regression of the disease or condition or at least one of its clinical or subclinical symptoms. The benefit to a patient to be treated is either statistically significant or at least perceptible to the patient and/or the physician.

Symptoms of active ulcerative proctitis include, but are not limited to, abdominal pain, diarrhea, rectal bleeding, sensation of incomplete emptying of the bowels, weight loss, fever, loss of appetite, tiredness, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia).

Unless otherwise specified, tap density is measured by the USP tapped density test <616>.

Formulations

The mesalamine (e.g., in powder form) is typically dispersed in a suppository base, such as hard fat. The suppository base can be an oily or fatty base. Conventional suppository bases which may be employed include theobroma oil, hard fats, glycerides of fatty acids, glycerol-gelatin bases, and mixtures thereof. Suitable hard fat bases include, but are no limited to, esterified mixtures of mono-, di- and triglycerides which are obtained by esterification of fatty acids (European Pharmacopoeia, 3rd edition 1997, Deutscher Apotheker Verlag Stuttgart. p. 1022; The United States Pharmacopoeia, USP 23, NF18). Such hard fats are commercially available, for example, under the name Witepsol® (e.g. Witepsol® H12). A preferred suppository base is hard fat (e.g., hard fat NF).

Preferred hard fat bases include, but are not limited to, hard fats containing a mixture of mono-, di- and triglycerides of saturated $C_{9-18}$ fatty acids. The hard fat base can comprise hard fats obtained by esterification of fatty acids of vegetable origin with glycerol, a macrogol ether containing 20 to 24 oxyethylene groups in the polyoxyethylene chain, e.g., polyoxyl-20-cetostearyl ether, and glycerides, e.g., glyceryl ricinoleate.

Other suitable suppository bases include, but are not limited to, cacao butter, lauric oil, beef tallow, hard fat, and any combination of any of the foregoing.

The drug load of the suppository is preferably 37 to 50%. According to one embodiment, the drug load ranges from about 37 to about 46%. According to another embodiment, the drug load ranges from about 39 to about 45%. According to yet another embodiment, the drug load ranges from about 41 to about 43%. For example, the suppository can contain about 1000 mg mesalamine dispersed in about 1300 to about 1500 mg of a suppository base (preferably hard fat).

The total weight of the suppository preferably ranges from about 2250 to about 2700 mg and more preferably from about 2250 to about 2500 mg. According to one embodiment, the suppository has a total weight ranging from about 2300 mg to about 2500 mg.

The suppository is preferably smooth torpedo-shaped.

The melting point of the suppository is generally sufficient to melt in the patient's body, and is typically no more than about 37° C.

Methods of Preparation

The mesalamine suppository of the present invention may be prepared as follows. The mesalamine is dispersed in a suppository base in molten form, which is then poured into a suitable mould, such as a PVC, polyethylene, or aluminum mould. For example, the mesalamine may be dispersed in the suppository base at a temperature of from about 35° C. to about 50° C. and preferably from about 40° C. to about 44° C. The mesalamine can be milled or sieved prior to incorporation into the suppository base.

If desired, further pharmaceutically acceptable auxiliaries, such as, for example, stabilizers, consistency-improving additives or auxiliaries which bring about a uniform distribution of the mesalamine in the suppository base, can be added. Optionally the suppositories may be coated, prior to packing, for example with cetyl alcohol, macrogol or polyvinyl alcohol and polysorbates to increase disintegration time or lubrication or to reduce adhesion on storage.

Preferably, the viscosity of a sample of the molten mesalamine dispersion is determined in-process for quality control. For example, the viscosity cut off may be about 5000 to about 10000 cps. According to one embodiment, batches of molten mesalamine dispersion having a viscosity of about 10000 cps or less would be considered acceptable while those having a viscosity over 10000 cps would not (and, therefore, may be discarded). According to another embodiment, batches of molten mesalamine dispersion having a viscosity of about 5000 cps or less would be considered acceptable.

The tap density of the mesalamine used to prepare the molten mesalamine dispersion is also preferably monitored before production to ensure that the tap density of the mesalamine is at least about 600 g/L and preferably from about 600 to about 800 g/L. Preferably, the mesalamine is not in the form of granules suitable for compaction into tablets. Rather, the mesalamine is preferably in the form of a powder of unagglomerated needle-shape crystals.

A sample suppository from each batch of suppositories produced is preferably tested by the dissolution method of the present invention for quality control. According to a preferred embodiment, a sample from each batch is tested to determine whether at least about 75 or 80% by weight of the mesalamine dissolves within 2 hours.

Methods of Treatment

The mesalamine suppository can be administered to treat ulcerative colitis, such as active ulcerative proctitis, in a patient in need thereof. Preferably, the mesalamine suppository is administered in sufficient quantity and frequency to reduce the symptoms of ulcerative colitis.

The mesalamine suppository can also be administered prophylactically to a patient at risk for ulcerative colitis (such as active ulcerative proctitis). Preferably, the mesalamine suppository is administered in sufficient quantity and frequency to delay or prevent the onset of symptoms of ulcerative colitis (e.g., to delay or prevent the onset of abdominal pain, diarrhea, rectal bleeding, weight loss, fever, loss of appetite, dehydration, anemia, or malnutrition, or any combination thereof).

In the above methods, the mesalamine suppository is preferably administered once a day and more preferably once a day at bedtime. The suppository is also preferably retained for one to three hours or longer, if possible. The treatment can be brief, for example, once daily for three to twenty-one days, or can be longer, for example, once daily for three to six weeks.

The following examples illustrate the invention without limitation. All percentages are by weight unless otherwise indicated.

EXAMPLE 1

The dissolution profiles of 1000 mg mesalamine suppositories (such as those prepared according to the procedure described below) were determined by three different methods (shown in Table 1 below using USP Apparatus #2). As discussed below, only the dissolution method of the present invention (method 2) produced consistent results.

TABLE 1

| Parameter | Method 1 | Method 2 | Method 3 |
|---|---|---|---|
| Phosphate buffer | 0.05 M | 0.2 M | 0.2 M |
| Temperature | 37° C. | 40° C. | 37° C. |
| Paddle rotation speed | 100 rpm | 125 rpm | 100 rpm |
| Sinker turns | 7 turns | 3 turns | 3 turns |
| pH | 7.5 | 7.5 | 7.5 |

Preparation of 1000 mg Mesalamine Suppositories 1000 mg mesalamine suppositories were prepared by the following procedure. Add 200.0 kg of hard fat NF (Witepsol® 15) to a mix tank. Begin heating the batch to 58-62° C. by recirculating steam through the tank jacket. The target temperature is 60° C. Begin mixing with the sweeps at 12 Hz as the product begins to melt. Continue heating to 58-62° C. (target 60° C.). Mix until the product is completely molten, increasing the sweeps to 60 Hz as the product melts. Mix for a minimum of 30 minutes, maintaining the temperature at 58-62° C. using the hot box (target 60° C.). Adjust the temperature of the batch to 40-44° C. by recirculating tap water at approximately 34-40° C. through the jacket. Maintain the batch at this temperature using the hot box (target 42° C.). While adjusting the temperature, shut off the sweeps, install the prop mixer with one 7"×7" blade and restart the sweeps to 60 Hz. Begin mixing with the prop at 12 Hz and adjust the sweeps to 30 Hz.

Slowly add 100.0 kg of mesalamine poswer USP to the mix tank. During the addition of the powder, slowly increase the sweeps to 35 Hz and the prop to 35 Hz as the product level in the tank increases, minimizing aeration. The addition of the powder must be performed over a 35 to 60 minute interval. The powder must be completely dispersed prior to mixing.

Mix for a minimum of 60 minutes. During the mix period, flush product through the bottom valve using a large pot. Continue flushing throughout the mixing interval until product appears visually uniform. Return the product to the mix tank.

Adjust the temperature of the batch to 43-45° C. by recirculating tap water at approximately 50-55° C. through the tank jacket or use the hot box, if necessary. Perform in-process sampling from the bottom valve of the tank taking approximately 600 g in a plastic beaker. Hook up the hot box and set it to hold the temperature of the batch at 43-45° C. Adjust the sweeps to 30-36 Hz and prop to 20-30 Hz to prevent aeration of the product.

Fill each mould. Remove 1 suppository per filling head (14 consecutive suppositories) every 25-35 minutes of operation. Fill weights of individual suppositories should be between 2.85 and 3.15 g.

Results

The dissolution profile of the 1000 mg mesalamine suppositories were determined by methods 1 and 2. The results are shown in Tables 2 and 3, respectively.

TABLE 2

| Time | Sample 1 | Sample 2 | Sample 3 |
|---|---|---|---|
| 10 min | 10.5 | 11.8 | 11.3 |
| 20 min | 22.4 | 20.9 | 21.8 |
| 30 min | 32.9 | 27.4 | 29.3 |
| 60 min | 54.6 | 42.8 | 44.5 |
| 90 min | 66.8 | 54.2 | 56.3 |
| 120 min | 77.2 | 63 | 65.9 |
| Average and SD (after 120 min) | | 68.70 (SD = 7.50) | |

TABLE 3

| Time | #1 | #2 | #3 | #4 | #5 | #6 | #7 | #8 | #9 | #10 | #11 | #12 | Average | SD |
|---|---|---|---|---|---|---|---|---|---|---|---|---|---|---|
| 60 min | 92.2 | 93 | 96.8 | 93.7 | 93.4 | 93.2 | 92.8 | 93.8 | 84 | 97.2 | 94.4 | 96.6 | 93.4 | 3.4 |
| 120 min | 97.3 | 97.6 | 98.1 | 97.9 | 95.5 | 98.6 | 98.1 | 97.9 | 97.9 | 98.1 | 97.9 | 98.4 | 97.8 | 0.8 |
| 240 min | 97.5 | 98.2 | 97.7 | 97.2 | 97 | 98.6 | 98.1 | 97.3 | 97.8 | 97.3 | 97.2 | 97.8 | 97.6 | 0.5 |

(SD = standard deviation)

The variability in the dissolution values after 120 minutes was significantly lower when measured by method 2 than when measured by method 1.

This low variability was further shown by dissolution tests using methods 2 and 3 performed on 1000 mg suppositories stored under normal (25° C. and 60% relative humidity) and accelerated (30° C. and 60% relative humidity) storage conditions. The results are provided in Tables 4 and 5, respectively, and show that method 2 provides reproducible dissolution values with minimal intra-lot and batch-to-batch variability.

TABLE 4

| Time | #1 | #2 | #3 | #4 | #5 | #6 | Average (%) | SD |
|---|---|---|---|---|---|---|---|---|
| Batch 1 (23.5 months, 25° C./60% RH) | | | | | | | | |
| 60 min | 97.8 | 96.8 | 98 | 99.2 | 98.2 | 98.6 | 98.1 | 0.8 |
| 120 min | 98.7 | 98.9 | 98.5 | 99.2 | 98.3 | 98.2 | 98.6 | 0.4 |
| 240 min | 98.3 | 98.5 | 98.1 | 98.6 | 97.5 | 987.7 | 98.1 | 0.4 |
| Batch 2 (14.5 months, 25° C./60% RH) | | | | | | | | |
| 60 min | 97.6 | 97.5 | 98.2 | 98.2 | 97.6 | 97.1 | 97.7 | 0.4 |
| 120 min | 97.1 | 97.5 | 97.9 | 97.9 | 98.3 | 97.2 | 97.7 | 0.5 |
| 240 min | 97.3 | 96.7 | 97.4 | 97.4 | 97.7 | 96.9 | 97.2 | 0.4 |
| Batch 3 (4 months, 25° C./60% RH) | | | | | | | | |
| 60 min | 98.5 | 96.7 | 91 | 92.2 | 96.7 | 98.2 | 95.6 | 3.2 |
| 120 min | 98.9 | 98.7 | 94.4 | 98.7 | 98.7 | 98.6 | 98.0 | 1.8 |
| 240 min | 98.5 | 98.2 | 96 | 97.3 | 97.7 | 97.8 | 97.6 | 0.9 |
| Batch 4 (2.5 months, 25° C./60% RH) | | | | | | | | |
| 60 min | 99.3 | 99.5 | 100.3 | 99.3 | 98.7 | 99.6 | 99.5 | 0.5 |
| 120 min | 98.8 | 98.9 | 99.9 | 99.4 | 98.4 | 99.6 | 99.2 | 0.6 |
| 240 min | 98.5 | 98.9 | 99.4 | 98.6 | 97.8 | 99.1 | 98.7 | 0.6 |

TABLE 4-continued

| Time | #1 | #2 | #3 | #4 | #5 | #6 | Average (%) | SD |
|---|---|---|---|---|---|---|---|---|
| Batch 5 (4.5 months, 25° C./60% RH) | | | | | | | | |
| 60 min | 100.8 | 101.7 | 101.3 | 101.4 | 101.3 | 101.4 | 101.3 | 0.3 |
| 120 min | 100.2 | 101.4 | 100.9 | 101 | 101.1 | 101.8 | 101.1 | 0.5 |
| 240 min | 100.2 | 100.5 | 100.5 | 100.5 | 100.8 | 101.1 | 100.6 | 0.3 |
| Batch 6 (4.5 months 25° C./60% RH) | | | | | | | | |
| 60 min | 99.7 | 99.8 | 99.3 | 101.1 | 100 | 100.3 | 100.0 | 0.6 |
| 120 min | 98.7 | 99.9 | 99.8 | 100.8 | 100.1 | 100.1 | 99.9 | 0.7 |
| 240 min | 98.5 | 99.4 | 99.7 | 100.6 | 99.8 | 99.4 | 99.6 | 0.7 |
| Batch 7 4.5 months, 25° /60% RH) | | | | | | | | |
| 60 min | 99.7 | 99.9 | 99.2 | 100.5 | 99.4 | 99.6 | 99.7 | 0.5 |
| 120 min | 100 | 99.7 | 99.6 | 100.4 | 99.1 | 99.7 | 99.8 | 0.4 |
| 240 min | 99.7 | 99 | 99 | 99.5 | 98.7 | 98.8 | 99.1 | 0.4 |
| Batch 8 (3.5 months, 30° C./60% RH) | | | | | | | | |
| 60 min | 100.8 | 100.3 | 100.7 | 101 | 101 | 100.7 | 100.8 | 0.3 |
| 120 min | 100.6 | 99.9 | 100.5 | 100.6 | 100.6 | 100.3 | 100.4 | 0.3 |
| 240 min | 99.9 | 99.2 | 99.9 | 100 | 100 | 99.5 | 99.8 | 0.3 |
| Batch 9 (3.5 months, 30° C./60% RH) | | | | | | | | |
| 60 min | 100 | 99.9 | 100.2 | 99.7 | 99.8 | 99.8 | 99.9 | 0.2 |
| 120 min | 99.7 | 99.4 | 100 | 99.4 | 100 | 99.5 | 99.7 | 0.3 |
| 240 min | 99.3 | 98.8 | 99.4 | 99 | 99.2 | 98.9 | 99.1 | 0.2 |
| Batch 10 (3.5 months 30° /60% RH) | | | | | | | | |
| 60 min | 99.3 | 98.9 | 99.9 | 99.8 | 99.6 | 99.3 | 99.5 | 0.4 |
| 120 min | 99.6 | 98.7 | 99.1 | 99.6 | 99.1 | 99.7 | 99.3 | 0.4 |
| 240 min | 99.1 | 98.4 | 98.6 | 99.2 | 98.7 | 99.1 | 98.9 | 0.3 |

TABLE 5

| | Sample No. (within batch) | | | | | | | |
|---|---|---|---|---|---|---|---|---|
| Batch | 1 | 2 | 3 | 4 | 5 | 6 | Average | SD |
| 11 | 101.5 | 102.4 | 102.5 | 101.5 | 100.9 | 100.6 | 101.6 | 0.8 |
| 6 months at 25° C./60% RH | | | | | | | | |
| 12 | 101.3 | 100.3 | 101.3 | 102.3 | 100.3 | 100.0 | 100.9 | 0.9 |
| 6 months at 25° C./60% RH | | | | | | | | |
| 13 | 100.4 | 99.7 | 98.6 | 100.3 | 98.8 | 99.8 | 99.6 | 0.8 |
| 6 months at 25° C./60% RH | | | | | | | | |
| 14 | 98.2 | 99.3 | 98.9 | 97.2 | 99.1 | 98.8 | 98.6 | 0.8 |
| 25 months at 25° C./60% RH | | | | | | | | |
| 15 | 92.4 | 98.4 | 97.6 | 97.3 | 96.7 | 92.0 | 95.7 | 2.8 |
| 16 months at 25° C./60% RH | | | | | | | | |
| 16 | 98.4 | 96.4 | 95.5 | 96.8 | 99.6 | 96.9 | 97.3 | 1.5 |
| 5 months at 25° C./60% RH | | | | | | | | |
| 17 | 99 | 98 | 97 | 100 | 99 | 81 | 95.7 | 7.3 |
| 23 months at 25° C./60% RH | | | | | | | | |
| 18 | 101 | 103 | 100 | 103 | 100 | 102 | 101.5 | 1.4 |
| 23 months at 25° C./60% RH | | | | | | | | |
| 19 | 101 | 102 | 101 | 103 | 100 | 102 | 101.5 | 1.0 |
| 20 months at 25° C./60% RH | | | | | | | | |
| 20 | 97 | 102 | 97 | 95 | 99 | 96 | 97.7 | 2.5 |
| 6 months at 30° C./60% RH | | | | | | | | |
| 21 | 94 | 94 | 72 | 81 | 91 | 106 | 89.7 | 11.8 |
| 6 months at 30° C./60% RH | | | | | | | | |
| 22 | 85 | 92 | 93 | 89 | 94 | 75 | 88.0 | 7.2 |
| 6 months at 30° C./60% RH | | | | | | | | |
| 23 | 85 | 90 | 97 | 91 | 96 | 85 | 90.7 | 5.2 |
| 6 months at 30° C./60% RH | | | | | | | | |
| 24 | 75 | 50 | 66 | 72 | 61 | 40 | 60.7 | 13.4 |
| 6 months at 30° C./60% RH | | | | | | | | |
| 25 | 73 | 97 | 60 | 89 | 87 | 81 | 81.2 | 13.1 |
| 6 months at 30° C./60% RH | | | | | | | | |

Samples from the three batches exhibiting the highest variability when measured according to method 3, i.e., batches 21, 24 and 25, were tested by method 2 for comparison. The results are shown in Table 6.

TABLE 6

| | Sample No. (within batch) | | | | | | | |
|---|---|---|---|---|---|---|---|---|
| Batch | 1 | 2 | 3 | 4 | 5 | 6 | Average | SD |
| 21 | 100 | 100 | 100 | 100 | 101 | 101 | 100.3 | 0.52 |
| 24 | 101 | 101 | 101 | 101 | 101 | 102 | 101.2 | 0.41 |
| 25 | 100 | 100 | 101 | 100 | 99 | 100 | 100.0 | 0.63 |

These results show that method 2 produced more reliable and less variable dissolution results than method 3.

EXAMPLE 2

The dissolution profiles of the 1000 mg mesalamine suppositories prepared in Example 1 were determined according to method 1 described in Example 1.

The results are shown in Table 7 below.

TABLE 7

| 1000 mg suppository |
|---|
| At 120 min, |
| Average: 73% + 10.3 (SD) |
| Range: 54.8%-97.1% |

EXAMPLE 3

The following experiment was conducted to determine if the tap density of the mesalamine powder starting material significantly affected the viscosity of the molten mixture used to form the suppository. Generally, a molten mixture having a viscosity greater than about 5000 to about 10000 cps was found to have flow problems during suppository filling and caused small entrapped air bubbles to be molded into the surface of the suppository resulting in an aesthetically less desirable product.

The tap density of several lots of mesalamine were determined by USP tapped density test <616> and are shown in Table 8 below.

TABLE 8

| Mesalamine Lot | Tapped Density (g/ml) |
|---|---|
| A | 0.81 |
| B | 0.72 |
| C | 0.68 |
| D | 0.39 |
| E | 0.68 |
| F | 0.46 |
| G | 0.60 |

Molten mixtures were prepared by the procedure described in Example 1 using mesalamine lots A, B, and E. The molten mixtures had the viscosities reported in Table 9 below.

TABLE 9

| Molten Mixture Lot No. | Mesalmine Lot | Mesalamine Tap Density (g/ml) | Viscosity (cps) |
|---|---|---|---|
| 1 | A | 0.81 | 429 |
| 2 | B | 0.72 | 468 |
| 3 | E | 0.68 | 1010 |

Molten mixtures prepared from combinations of mesalamine lots C-G were prepared and had the viscosities reported in Table 10 below. The individual tap densities of each mesalamine lot were used to calculate a composite tapped density (CTD) based on the amount of each lot. The calculated CTD can be expressed by the following equation:

$$(CDF)_1 + (CDF)_2 + \ldots (CDF)_n = CTD$$

where CTD=composite tapped density; CDF=contributed density factor=% of total drug used/100×TD; TD=measured tapped density; and n=number of drug lots used.

TABLE 10

| Molten Mixture Lot No. | Mesalamine Lot | Measlamine used (Kg) | TD (g/ml) | CTD (g/ml) | Viscosity (cps) |
|---|---|---|---|---|---|
| 4 | C | 82.5 | 0.68 | | |
| | D | 17.5 | 0.37 | 0.62 | 1680 |
| 5 | D | 61.0 | 0.37 | | |
| | E | 17.0 | 0.68 | | |
| | F | 22.0 | 0.46 | 0.44* | 13300 |
| 6 | G | 100.0 | 0.60 | 0.60 | 1730 |

*Note:
Accuracy of the CTD of the 3 mesalamine lots used was confirmed by measuring the tap density of a separate mesalamine powder blend at the same ratio. The result was 0.43 g/ml compared to 0.44 g/ml.

The density-viscosity data from Tables 9 and 10 were combined and plotted (FIG. 1) to assess the correlation for these two parameters. These data show a definite rank-order inverse relationship, with a correlation coefficient of 0.9743. Notably, a reduction in the CTD from 0.60 g/ml to 0.44 g/ml resulted in a 7 fold increase in viscosity from 1730 cps to 13300 cps (see molten mixture lot nos. 5 and 6 in Table 10).

EXAMPLE 4

Figure 2:
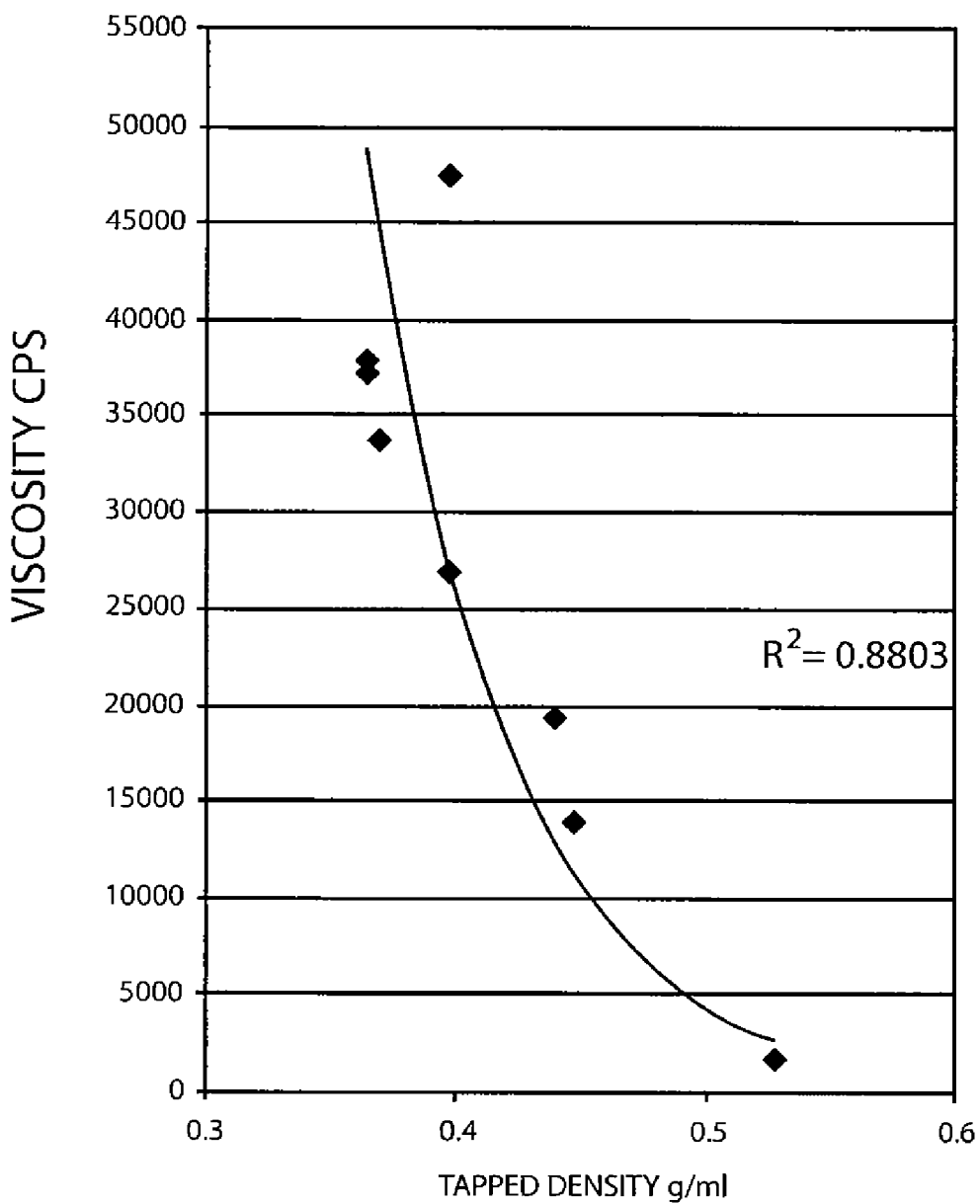
FIG. 2 is a graph showing the viscosity of the molten mixtures prepared in Example 4 versus the tap densities of the mesalamine used to prepare the molten mixtures.

The procedure described in Example 3 was repeated with mesalamine lot nos. 1-8 shown in Table 11 below. The results are shown in Table II and FIG. 2. From the correlation curve in FIG. 2, a viscosity of 5000 cps corresponds to a tap density of about 0.50 g/ml.

TABLE 11

| Mesalamine Lot No. | Tap Density (g/ml) | Viscosity (cps) |
|---|---|---|
| 1 | 0.45 | 13845 |
| 2 | 0.53 | 1755 |
| 3 | 0.44 | 19500 |
| 4 | 0.36 | 37100 |
| 5 | 0.40 | 47500 |
| 6 | 0.40 | 26910 |
| 7 | 0.36 | 37830 |
| 8 | 0.37 | 33735 |

The correlation of density to viscosity is essentially rank-order and demonstrates an inverse relationship of the two parameters (correlation coefficient=0.8803).

Figure 3:
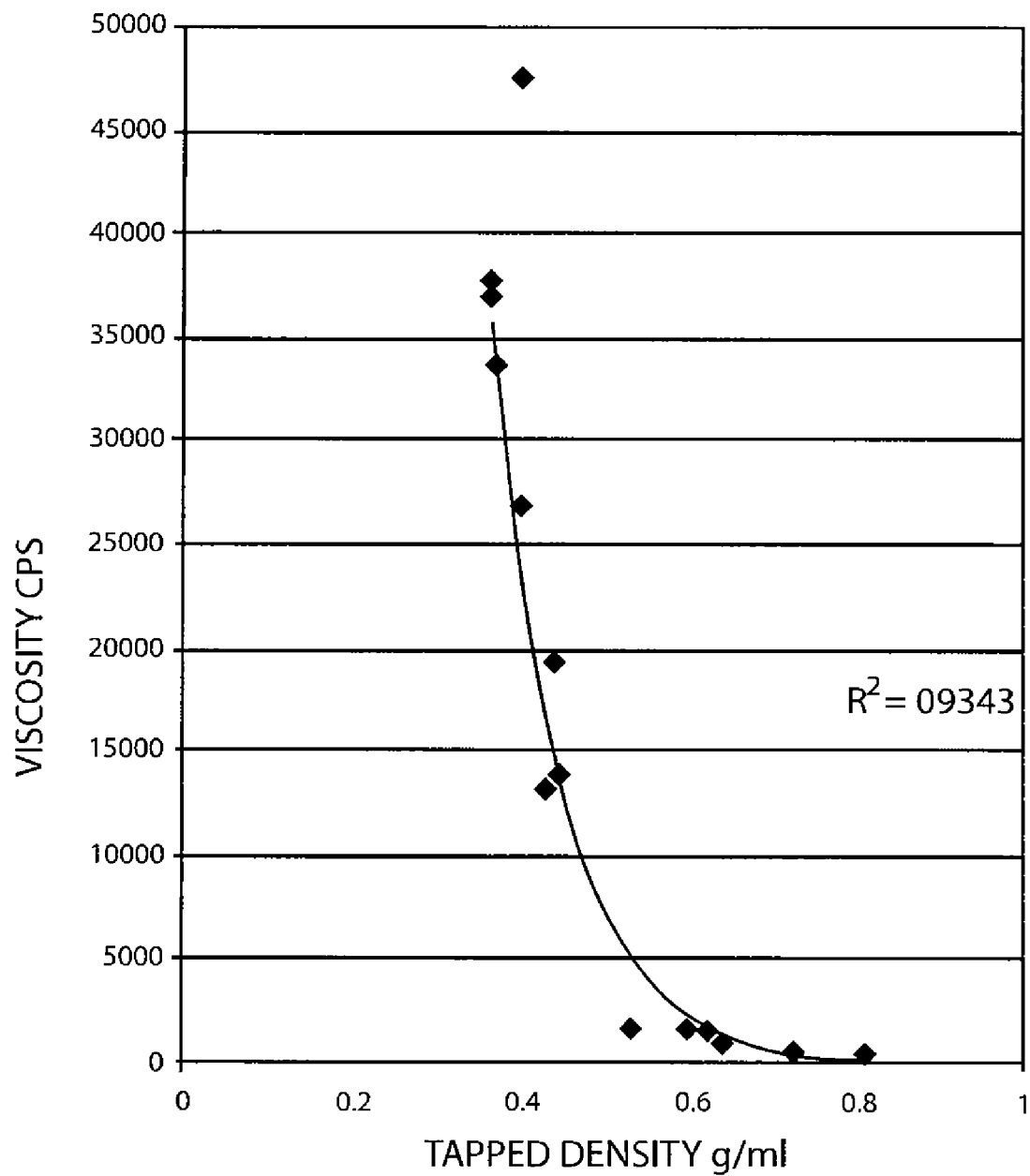
FIG. 3 is a graph showing the viscosity of the molten mixtures prepared in Examples 3 and 4 versus the tap densities of the mesalamine used to prepare the molten mixtures.

The tap density and viscosity data from Examples 3 and 4 (Tables 9-11) were combined and are shown graphically in FIG. 3. The combined data clearly show the strong correlation (correlation coefficient=0.9343) between the tap density of mesalamine powder and its effect on the in-process viscosity of the drug-hard fat dispersions.

EXAMPLE 5

1 g mesalamine suppositories using Witepsol® H-15 or Witepsol® H-12 (hard fat NF) as the suppository base were prepared by the procedure described in Example 1 at drug loads of 33, 37, 42, and 44%. All the suppositories released at least 75% by weight of the mesalamine contained in the suppository within 2 hours of dissolution as measured with USP Apparatus #2 at 40° C., a paddle rotation speed of 125 rpm, and 3 sinker turns in 0.2 M phosphate buffer at a pH of 7.5 (method #2 of Table #1).

Figure 4:
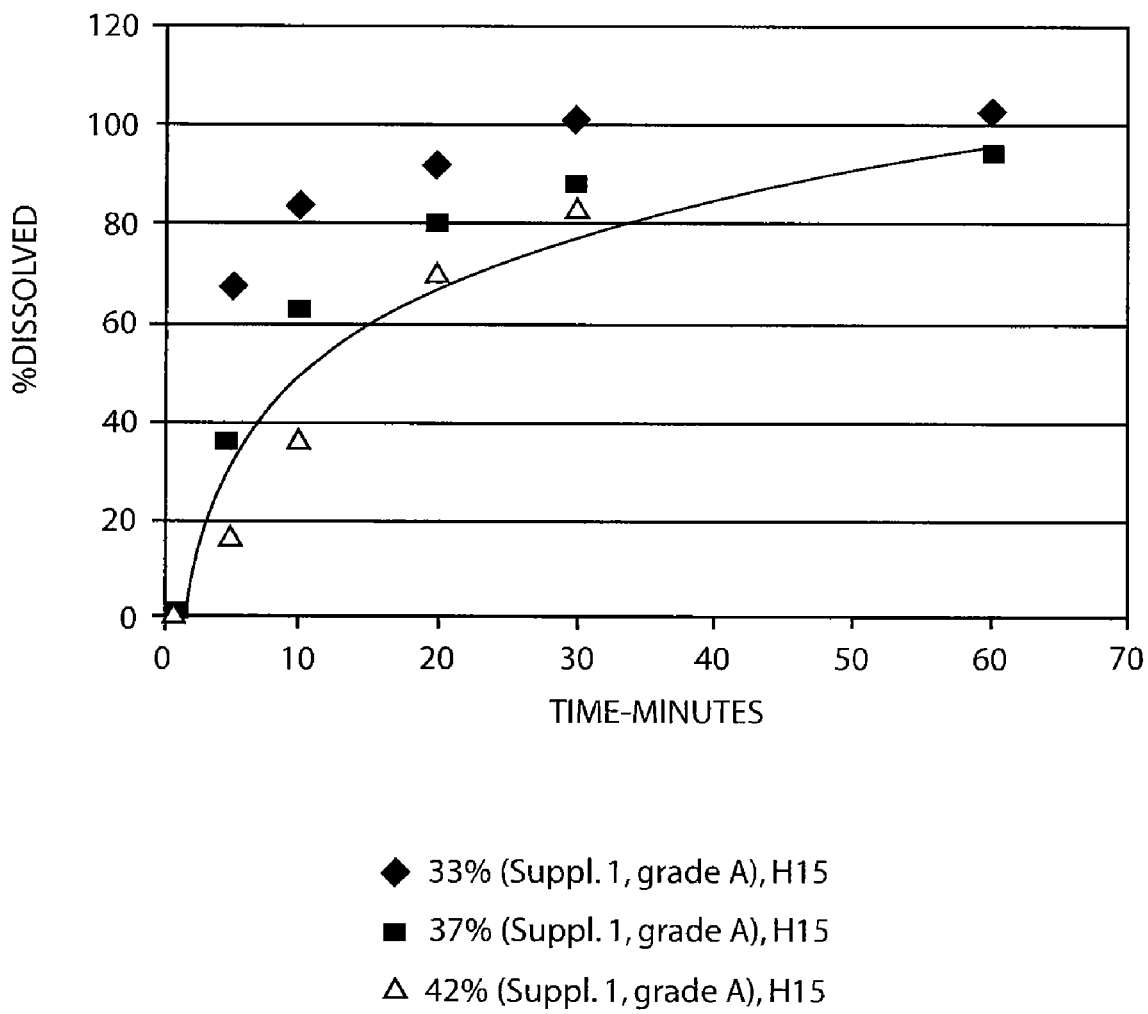
FIGS. 4-9 show the dissolution profiles of mesalamine suppositories having drug loads of 33, 37, and 42% prepared from mesalamine having a tap density of 680 or 730 g/L and hard fat having an ascending melting point of 32 to 33.5° C. (Witepsol® H-12) or 33.5 to 35.5° C. (Witepsol® H-15).
Figure 5:
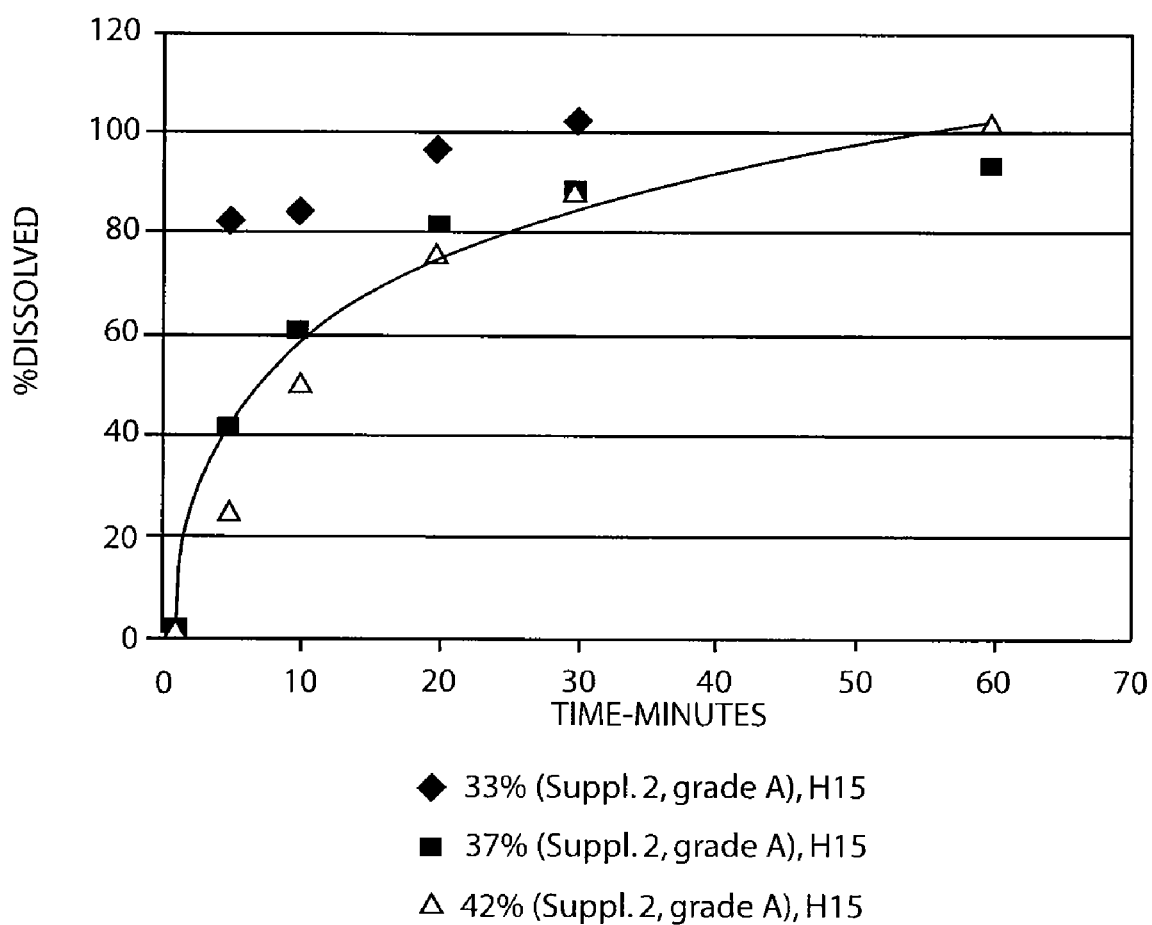

FIGS. 4 and 5 show the dissolution profiles of mesalamine suppositories having drug loads of 33, 37, and 42% prepared from mesalamine having a tap density of 680 g/L and Witepsol® H-15.

Figure 6:
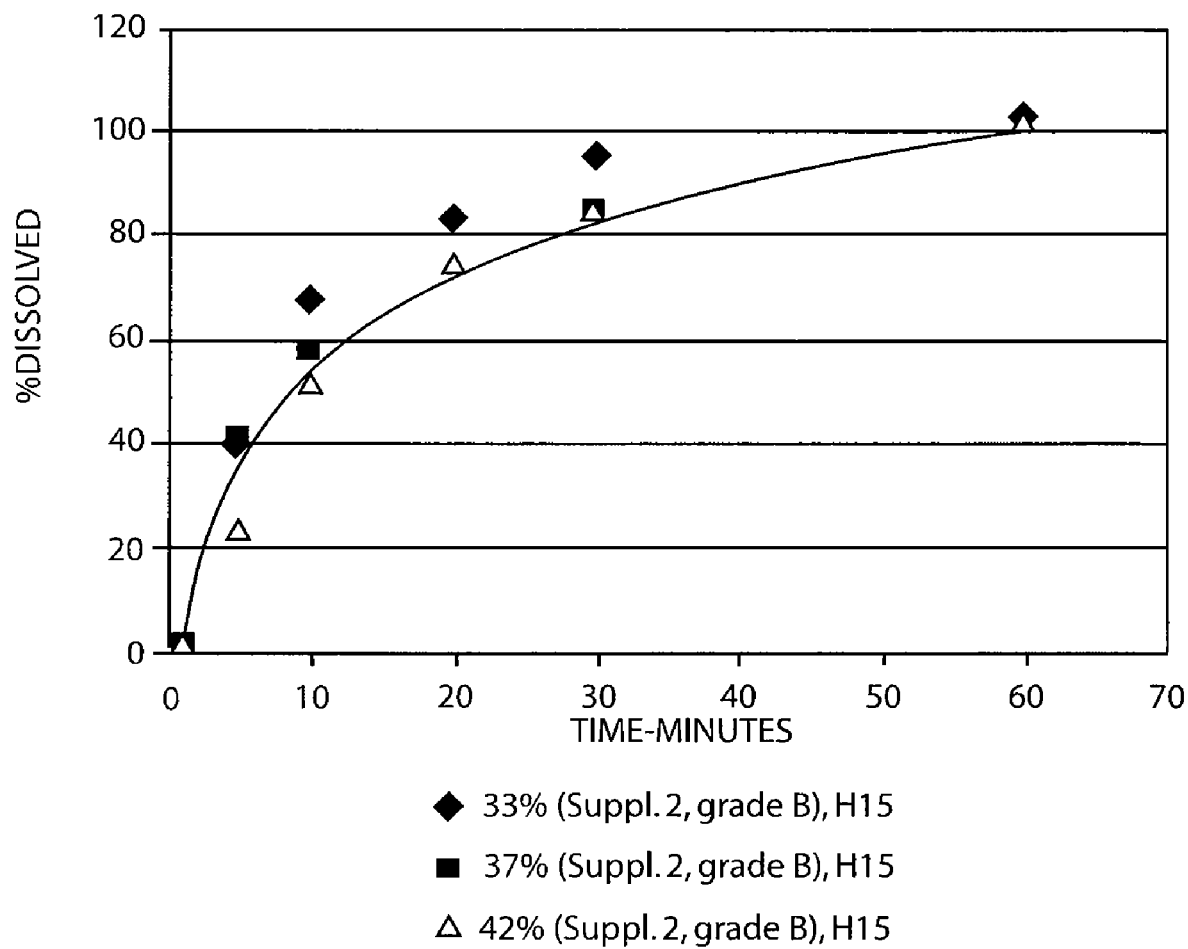

FIG. 6 shows the dissolution profiles of mesalamine suppositories having drug loads of 33, 37, and 42% prepared from mesalamine from Supplier 2, Grade B, having a tap density of 730 g/L and Witepsol® H-15.

The in-process molten mixtures of mesalamine and hard fat used in the preparation of the suppositories described above with respect to FIGS. 4 to 6 had the viscosities reported in Table 12 below. Suppositories could not be made from Grades C and D from supplier 2. Grades C and D were designed for compression of the mesalamine into tablets and were found to be unsuitable for the preparation of a suspension in hard fat as required for the preparation of the suppository.

TABLE 12

| Source | Tap Density g/L | Drug Load (% w/w) | Dispersion Viscosity (Cps) |
|---|---|---|---|
| Supplier 1 | 0.68 | 33 | 694 |
| | | 37 | 1131 |
| | | 42 | 2512 |

TABLE 12-continued

| Source | Tap Density g/L | Drug Load (% w/w) | Dispersion Viscosity (Cps) |
|---|---|---|---|
| Supplier 2, grade A | 0.68 | 33 | 595 |
|  |  | 37 | 1084 |
|  |  | 42 | 2553 |
| Supplier 2, grade B | 0.73 | 33 | 515 |
|  |  | 37 | 845 |
|  |  | 42 | 1911 |
| Supplier 2, grade C | 0.58 | 33 | Too Viscous |
| Supplier 2, grade D | 0.91 | 33 | Poor Dispersion |

Figure 7:
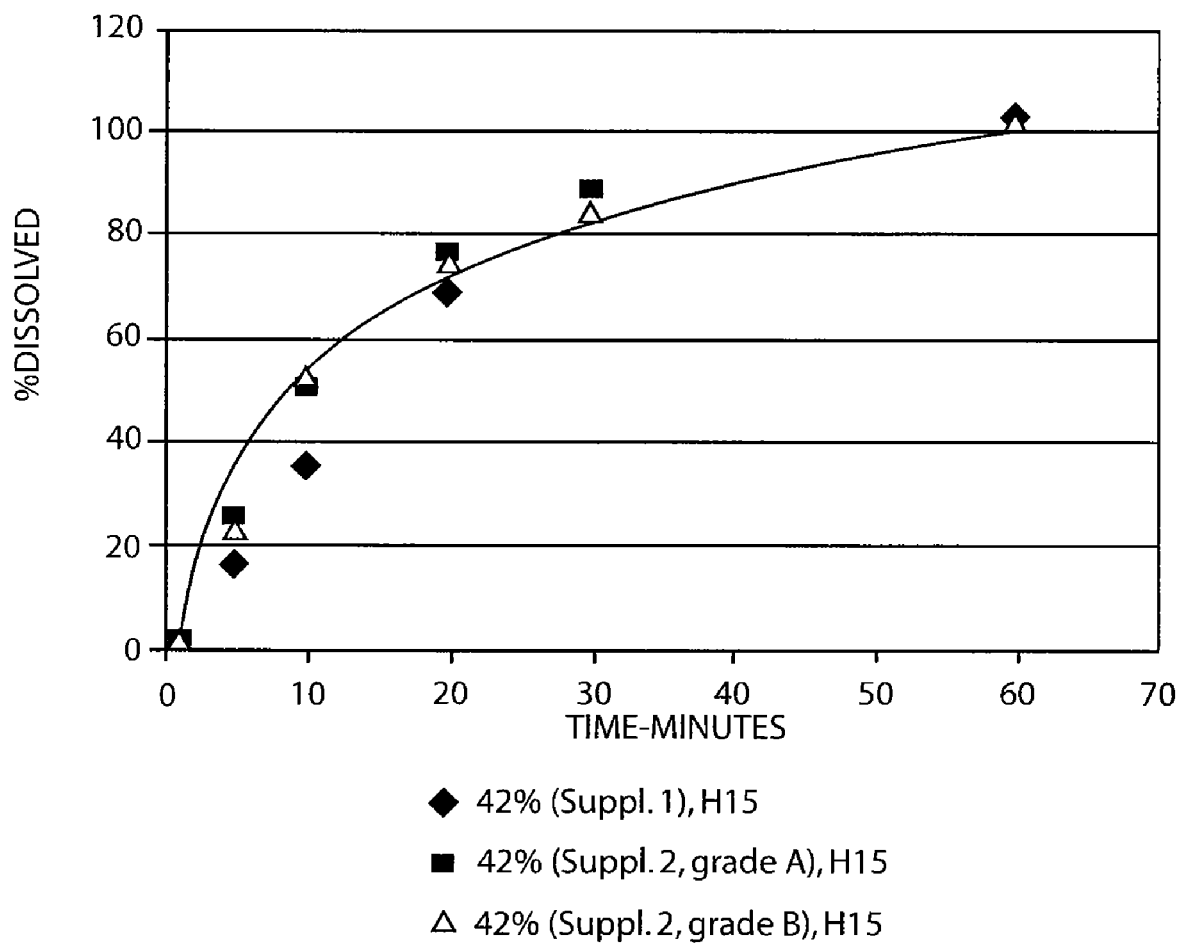

FIG. 7 shows the dissolution profiles of mesalamine suppositories having a drug load of 42% prepared from mesalamine having a tap density of 680 g/L (supplied by Suppliers 1 and 2) or 730 g/L (Supplier 2, grade B) and Witepsol® H-15.

Figure 8:
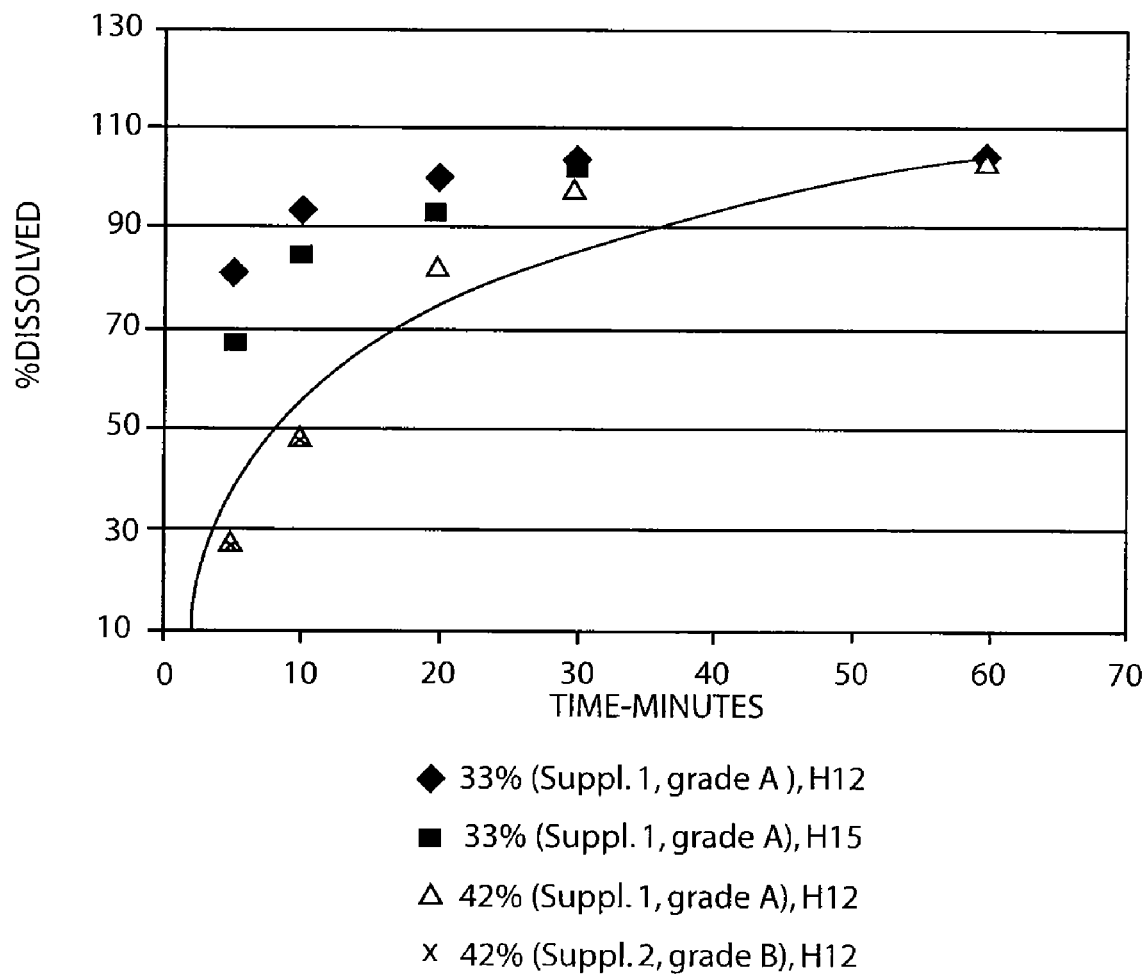

FIG. 8 shows the dissolution profiles of mesalamine suppositories having drug loads of 33% and 42% prepared from mesalamine having a tap density of 680 g/L from supplier 1 and Witepsol® H-12 (ascending melting point of 32 to 33.5° C.) or Witepsol® H-15 (ascending melting point of 33.5 to 35.5° C.). It also compares suppositories having drug loads of 42% prepared with a mesalamine from supplier 2 having a tap density of 730 g/ml manufactured using Witepsol® H-12 (ascending melting point of 32 to 33.5° C.).

Figure 9:
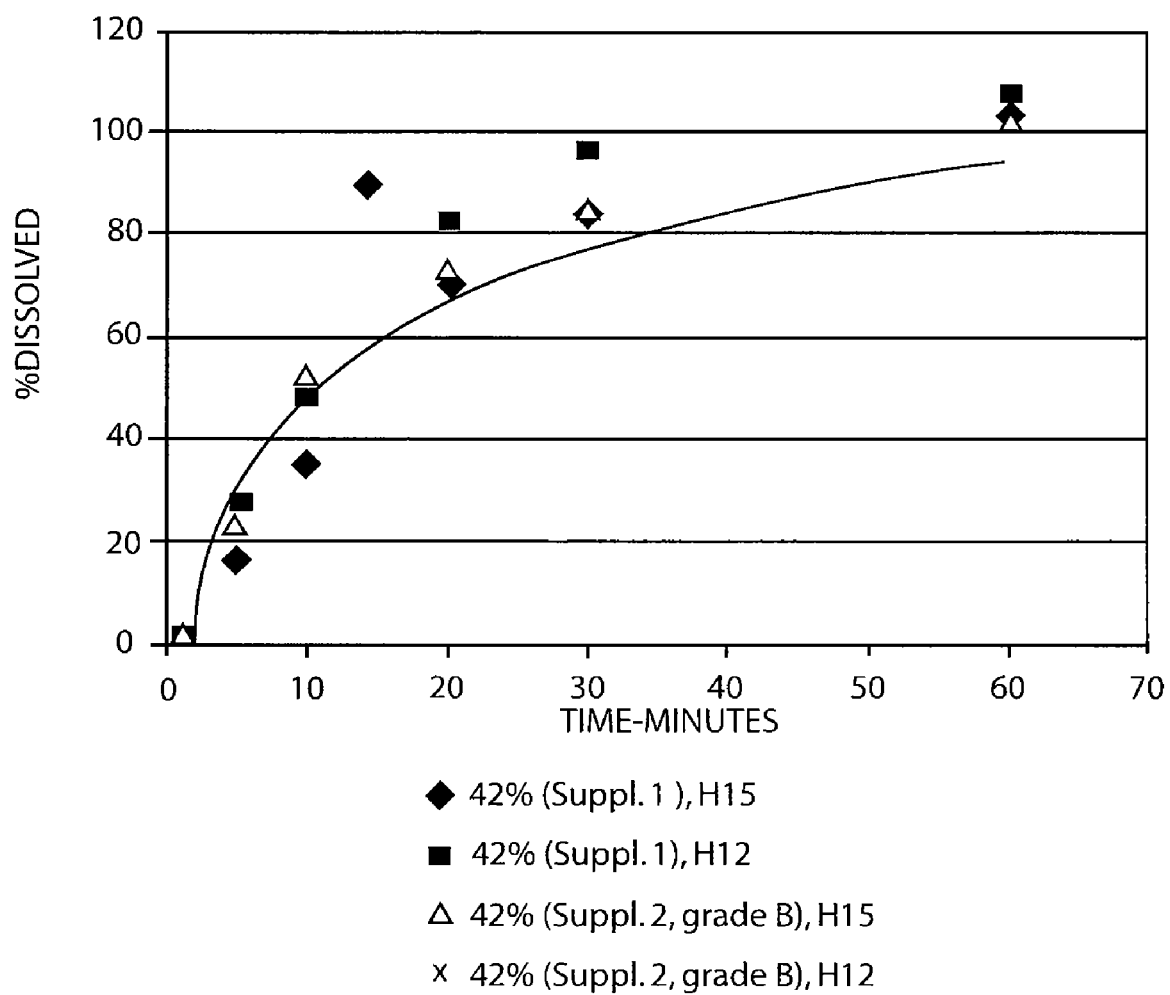

FIG. 9 shows the dissolution profiles of mesalamine suppositories having a drug load of 42% prepared from mesalamine having a tap density of 680 g/L (Supplier 1) or 730 g/L (Supplier 2, grade B) and Witepsol® H-12 or Witepsol® H-15.

Figure 10:
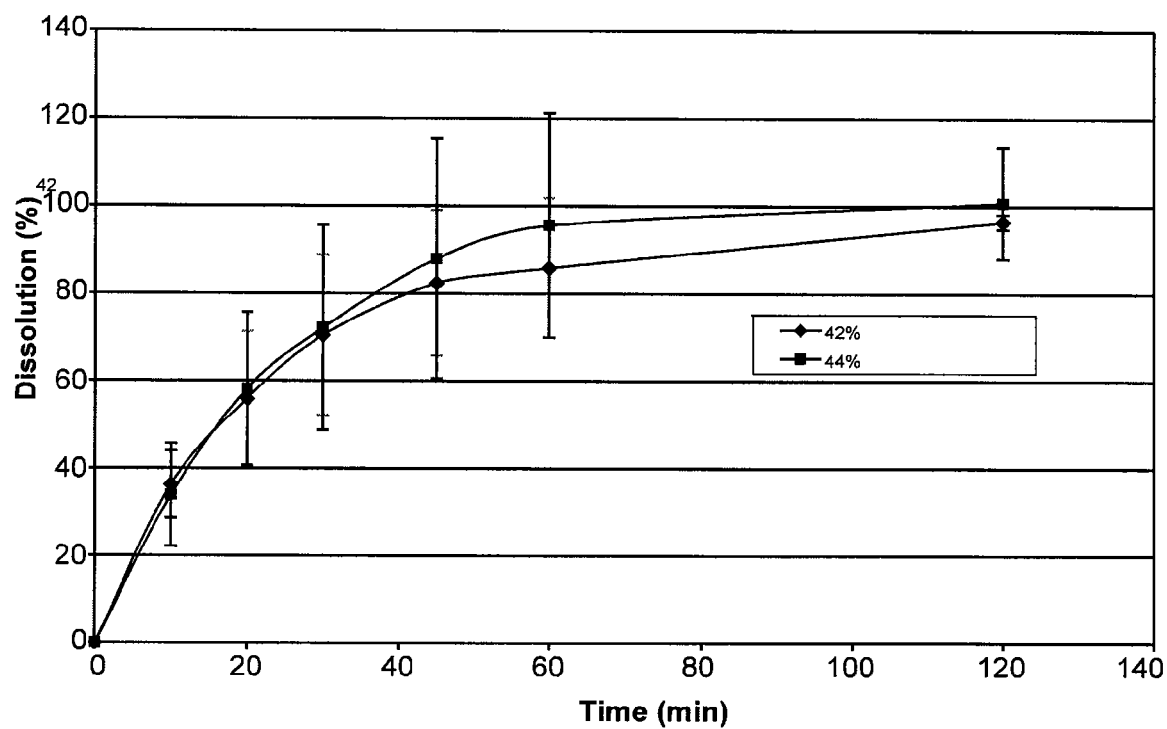
FIG. 10 shows the dissolution profiles of mesalamine suppositories having drug loads of 42 and 44% prepared from mesalamine having a tap density of 730 g/L and hard fat having an ascending melting point of 32 to 33.5° C. (Witepsol® H-12).

FIG. 10 shows the dissolution profiles of mesalamine suppositories from a larger scale batch having drug loads of 42 and 44% prepared from mesalamine having a tap density of 730 g/L (Supplier 2, grade B) and Witepsol® H-12.

EXAMPLE 6

High Density 1000 mg Mesalamine Suppositories 1 g mesalamine suppositories, each containing 1000 mg mesalamine (USP) and 1381 mg Witepsol® H-12 (hard fat NF), were prepared according to the following procedure.

The hard fat (Witepsol® H-12, 65.25 kg) is melted by charging it into a kettle, which is operated in automatic mode with a tank temperature of 75° C., a melting temperature of 60° C., a cooling water temperature of 48° C., a cooling air temperature of 44° C., a holding a T melting of 45 minutes, a mixing at T melting of 15 minutes, and a holding at 256 rpm for 60 minutes. When the temperature reaches 40-44° C., the mixing speed is between 60-80 rpm, and the water heating tank temperature is 71-79° C., the mesalamine from Supplier 2, grade B is slowly added over a period of 50 to 70 minutes with constant mixing at 230-270 rpm. The solution is then mixed for 55 to 65 minutes (set point of 60 minutes) at 230-270 rpm. After the mixing time, the mixing speed is adjusted to 168-180 rpm (set point of 175 rpm).

Moulds are then filled, each mould containing 2.33-244 g of the solution. The moulds are then cooled for 5 to 10 minutes at 20° C.

1 g suppositories heat sealed in PVC/PE containers (2.3 mL capacity per cavity) were stored for at 25±2° C. and 60±5% relative humidity for 3 months. The suppositories were found to be stable and release at least 80% by weight of the mesalamine contained in the suppository within 2 hours of dissolution as measured with USP Apparatus #2 at 40° C., a paddle rotation speed of 125 rpm, and 3 sinker turns in 0.2 M phosphate buffer at a pH of 7.5.

All non-patent references, patents and patent applications cited and discussed in this specification are incorporated herein by reference in their entirety and to the same extent as if each was individually incorporated by reference.

We claim:

1. A mesalamine rectal suppository comprising from about 850 to about 1150 mg of mesalamine and a fatty base, wherein the mesalamine has a tap density ranging from about 600 to about 800 g/L (as measured by USP <616>), the drug load of the suppository ranges from 35% to 46%, and the suppository releases at least 75% by weight of the mesalamine within 2 hours of dissolution as measured with USP Apparatus #2 at 40° C., a paddle rotation speed of 125 rpm, and 3 sinker turns in 0.2 M phosphate buffer at a pH of 7.5.

2. The mesalamine suppository of claim 1, wherein the amount of mesalamine ranges from about 950 to about 1050 mg.

3. The mesalamine suppository of claim 1, wherein the fatty base is hard fat.

4. The mesalamine suppository of claim 1, wherein the fatty base has an ascending melting point ranging from 32 to 33.5° C.

5. The mesalamine suppository of claim 1, wherein the fatty base has an ascending melting point from 33 to 35.5° C.

6. The mesalamine suppository of claim 4, the base is hard fat.

7. The mesalamine suppository of claim 5, the fatty base is hard fat.

8. The mesalamine suppository of claim 1, wherein the drug load ranges from about 39 to about 45%.

9. The mesalamine suppository of claim 8, wherein the drug load ranges from about 41 to about 43%.

10. The mesalamine suppository of claim 1, wherein the suppository releases at least 80% by weight of the mesalamine within 2 hours of dissolution as measured with USP Apparatus #2 at 40° C., a paddle rotation speed of 125 rpm, and 3 sinker turns in 0.2 M phosphate buffer at a pH of 7.5.

11. The mesalamine suppository of claim 1, wherein the suppository releases at least 80% by weight of the mesalamine within 1 hour of dissolution as measured with USP Apparatus #2 at 40° C., a paddle rotation speed of 125 rpm, and 3 sinker turns in 0.2 M phosphate buffer at a pH of 7.5.

12. The mesalamine suppository of claim 1, wherein the suppository releases at least 90% by weight of the mesalamine within 30 minutes of dissolution as measured with USP Apparatus #2 at 40° C., a paddle rotation speed of 125 rpm, and 3 sinker turns in 0.2 M phosphate buffer at a pH of 7.5.

13. A method of treating active ulcerative proctitis in a patient in need thereof comprising administering the mesalamine rectal suppository of claim 1 to the patient.

14. The method of claim 13, wherein the mesalamine rectal suppository is administered once a day.

15. The method of claim 14, wherein the mesalamine rectal suppository is administered once a day at bedtime.

16. The mesalamine suppository of claim 1, wherein the suppository is a moulded suppository.

* * * * *